(12) United States Patent
Zhang et al.

(10) Patent No.: US 12,171,897 B2
(45) Date of Patent: Dec. 24, 2024

(54) STERILIZATION AND AIR PURIFICATION CONTROL SYSTEM AND MOUNTING STRUCTURE OF WASTE DISPOSER

(71) Applicant: Zhejiang Rosun Kitchen & Bath Technology Co., Ltd., Zhejiang (CN)

(72) Inventors: Jin Zhang, Zhejiang (CN); Yu Zhang, Zhejiang (CN)

(73) Assignee: Zhejiang Rosun Kitchen & Bath Technology Co., Ltd., Zhejiang (CN)

( * ) Notice: Subject to any disclaimer, the term of this patent is extended or adjusted under 35 U.S.C. 154(b) by 799 days.

(21) Appl. No.: 17/405,038

(22) Filed: Aug. 18, 2021

(65) Prior Publication Data

US 2022/0387648 A1    Dec. 8, 2022

(30) Foreign Application Priority Data

Jun. 7, 2021  (CN) .......................... 202110636752.7

(51) Int. Cl.
*A61L 2/20* (2006.01)
*A61L 2/24* (2006.01)

(52) U.S. Cl.
CPC .............. *A61L 2/24* (2013.01); *A61L 2/202* (2013.01); *A61L 2209/11* (2013.01); *A61L 2209/12* (2013.01)

(58) Field of Classification Search
CPC ........ A61L 2/24; A61L 2/202; A61L 2209/11; A61L 2209/12; A61L 2202/11; A61L 2202/122; A61L 2202/14; A61L 2209/111; A61L 2209/212; A61L 9/22; A61L 11/00; A61L 2/14; E03C 1/12
USPC .......................................................... 422/119
See application file for complete search history.

(56) References Cited

FOREIGN PATENT DOCUMENTS

| CN | 202798109 U | * | 3/2013 | |
| CN | 107514704 A | * | 12/2017 | .............. F24F 13/08 |
| CN | 107747340 A | * | 3/2018 | .............. E03C 1/264 |
| WO | WO-2019010722 A1 | * | 1/2019 | .............. B09B 3/00 |

* cited by examiner

*Primary Examiner* — Huy Tram Nguyen
(74) *Attorney, Agent, or Firm* — JCIP GLOBAL INC.

(57) ABSTRACT

A sterilization and air purification control system and a mounting structure of a waste disposer include a bottom mounting housing and a disposer main machine and a sterilization module. The sterilization module includes an ozone generator driver, a negative oxygen ion generator and an exhaust mechanism. The bottom mounting housing is an accommodating housing and is detachably mounted at a bottom portion of the disposer main machine, an outer edge of the bottom mounting housing is provided with a light strip, the exhaust mechanism is fixedly connected to an inside of one side surface of the bottom mounting housing, and the exhaust mechanism communicates with inner and outer sides of the bottom mounting housing.

10 Claims, 5 Drawing Sheets

STERILIZATION AND AIR PURIFICATION CONTROL SYSTEM AND MOUNTING STRUCTURE OF WASTE DISPOSER

CROSS-REFERENCE TO RELATED APPLICATION

This application claims the priority benefit of China application serial no. 202110636752.7, filed on Jun. 7, 2021. The entirety of the above-mentioned patent application is hereby incorporated by reference herein and made a part of this specification.

BACKGROUND

Technical Field

The present invention relates to the field of intelligent household products, in particular to a sterilization and air purification control system and a mounting structure of a waste disposer.

Description of Related Art

An existing kitchen cabinet connected with a sewer is a semi-enclosed space, high in air humidity, and easy to propagate bacteria and generate mould to result in unpleasant odor in a kitchen, and therefore, a sterilization device capable of realizing effective sterilization is needed.

The disinfection of a kitchen cabinet is generally implemented by virtue of ultraviolet and ozone. Compared with ultraviolet, ozone disinfection is performed without dead angles. An existing waste disposer adopts ultraviolet to disinfect and is not humanized enough, and therefore, it is necessary to effectively combine the waste disposer with a sterilization module to provide a user better use experience and safety guarantee.

SUMMARY

In order to overcome above-mentioned defects in an existing technical solution, the present invention provides a sterilization and air purification control system and a mounting structure of a waste disposer.

A specific technical solution is described as follows.

Provided are a sterilization and air purification control system and a mounting structure of a waste disposer, including a bottom mounting housing, a disposer main machine and a sterilization module. The sterilization module includes an ozone generator driver, a negative oxygen ion generator and an exhaust mechanism, the bottom mounting housing is an accommodating housing and is detachably mounted at a bottom portion of the disposer main machine, an outer edge of the bottom mounting housing is provided with a light strip, the exhaust mechanism is fixedly connected to an inside of one side surface of the bottom mounting housing, and the exhaust mechanism communicates with inner and outer sides of the bottom mounting housing. A main control panel, an electric control subpanel, a starting capacitor and the sterilization module are mounted in the bottom mounting housing, and the electric control subpanel, the starting capacitor, the sterilization module and the light strip are all electrically connected to the main control panel.

Preferably, the main control panel is connected with an overload protector, a fan power interface, a light strip power interface and a motor power interface.

Preferably, the electric control subpanel includes a buzzer, a remote control receiving module and a toggle switch, and the toggle switch has three gears.

Preferably, the three gears respectively represent that "a sterilization function is switched off", "a remote control function is switched on or off", and "the sterilization function is switched on to remotely control the sterilization module to be switched on or off".

Preferably, the light strip is connected to the light strip power interface by a conductive wire, and the light strip has three working modes including a blue marquee state, a green breath light state and a red constant light state.

Preferably, when the disposer main machine is started, the buzzer makes a sound, and the light strip enters the blue marquee state; after the disposer main machine is halted, the overload protector works, the main control panel controls a motor of the disposer main machine to forwards and reversely rotate for five times and then stop, then, the light strip enters the red constant light state and is kept in the state for 1 minute, and meanwhile, the buzzer constantly makes sounds for 1 minute; and after the disposer main machine is shut down, the light strip enters the green breath light state, and when the sterilization module is started, the buzzer makes a sound and the sterilization module runs for 5 minutes.

Preferably, the exhaust mechanism includes an exhaust chamber, an exhaust fan and an ozone generator cell, the exhaust fan and the ozone generator cell are both mounted in the exhaust chamber, the exhaust fan is capable of taking air in the bottom mounting housing out of the bottom mounting housing through a first air outlet, the first air outlet is located in a bottom surface, corresponding to the exhaust chamber, of the bottom mounting housing, the ozone generator cell is electrically connected to the ozone generator driver, and the exhaust fan is connected to the fan power interface by a conductive wire.

Preferably, a bottom surface, close to the negative oxygen ion generator, of the bottom mounting housing is provided with a second air outlet.

The present invention has the beneficial effects as follows.

1. By using the exhaust mechanism, ozone may be effectively exhausted to be full of a kitchen cabinet, and air flow in the kitchen cabinet is enhanced, so that effective sterilization is realized.

2. By combining the disposer main machine with an electric control system of the sterilization module, work interaction between the disposer main machine and the sterilization module is realized.

3. By arranging a toggle switch and a light strip reminder, higher humanization is achieved, and more choices and better use experience are brought for a user.

To make the aforementioned more comprehensible, several embodiments accompanied with drawings are described in detail as follows.

DESCRIPTION OF THE EMBODIMENTS

Embodiments of the present invention will be described in detail below, and the following embodiments are exemplary and are intended to explain the present invention, but cannot be understood as limitations to the present invention.

Figure 1:
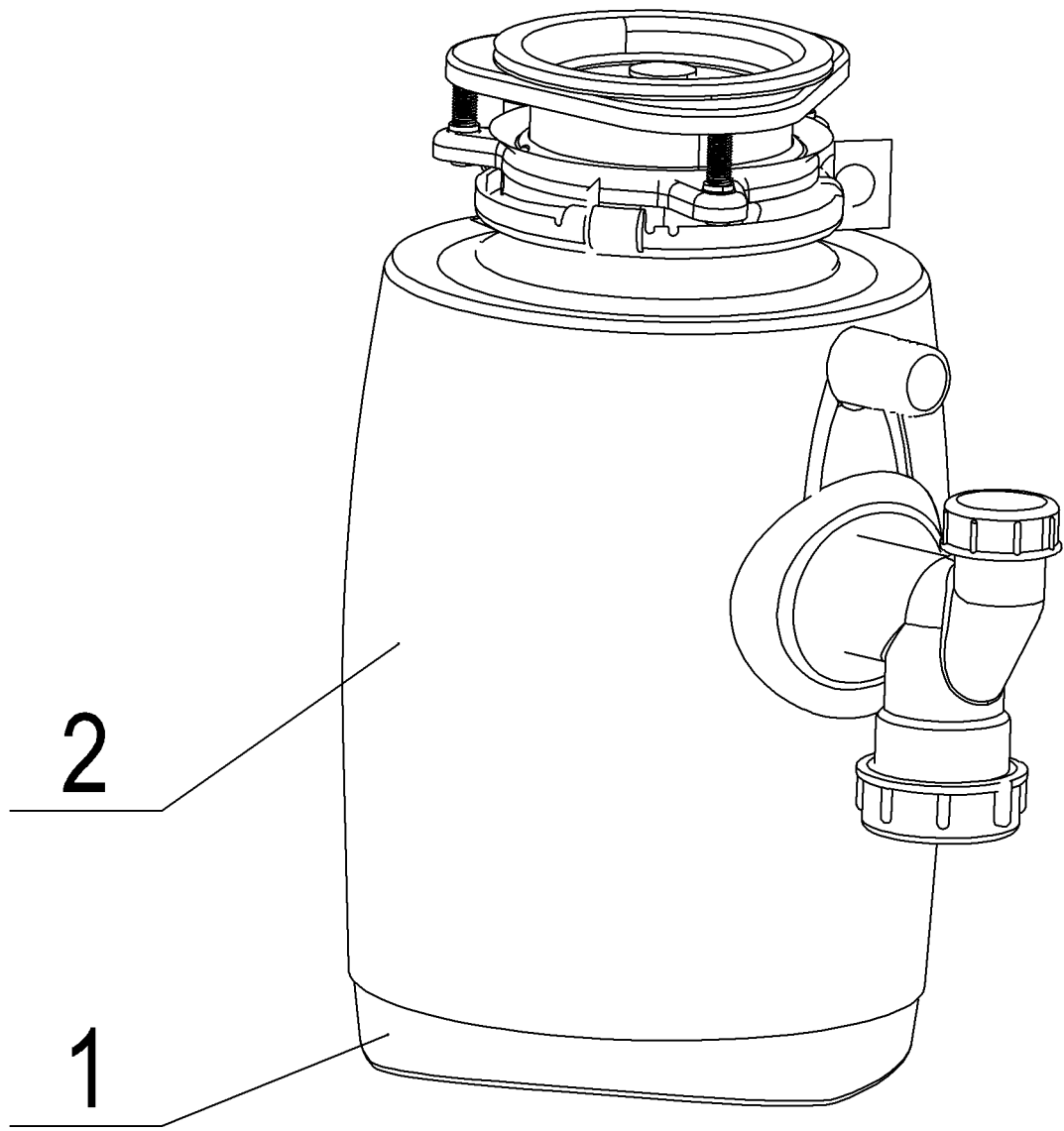
FIG. 1 is a schematic diagram showing an assembly state of a disposer main machine and a bottom mounting housing of a sterilization control system of a waste disposer according to the present invention.
Figure 2:
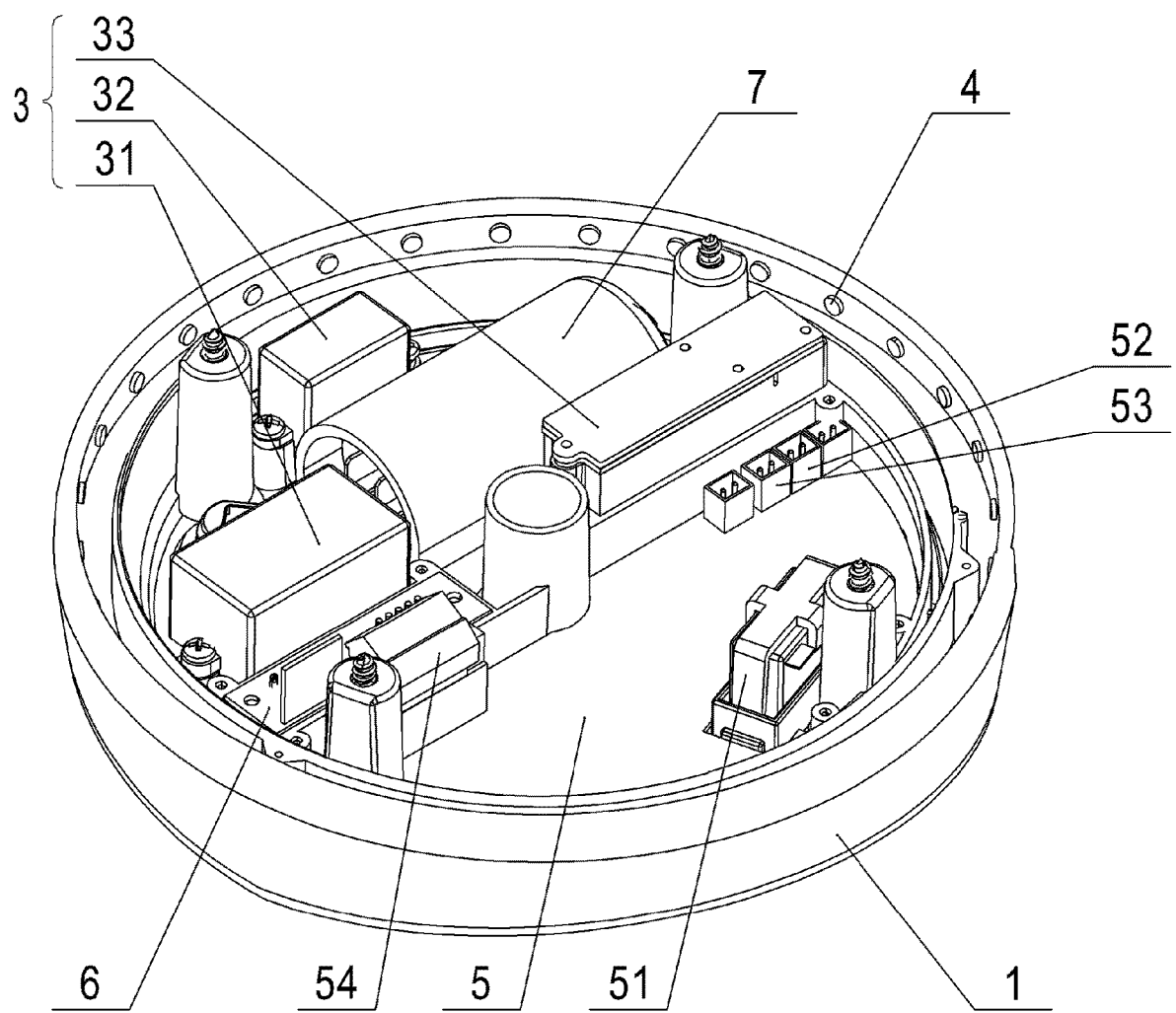
FIG. 2 is a schematic diagram showing the mounting of each structure in the sterilization control system of the waste disposer according to the present invention.
Figure 3:
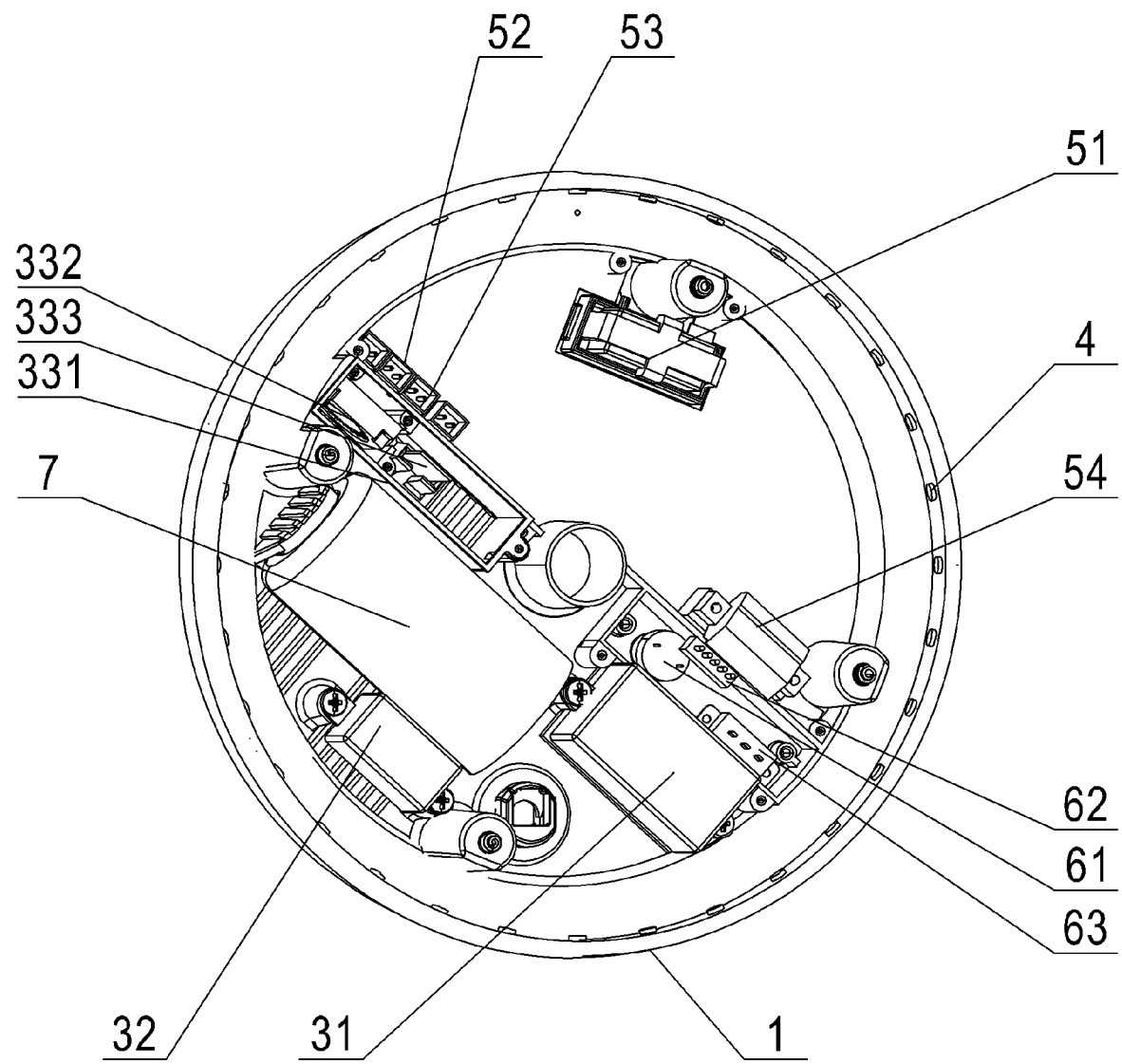
FIG. 3 is a schematic diagram showing specific structures of an exhaust mechanism and an electric control subpanel of the sterilization control system of the waste disposer according to the present invention.
Figure 4:
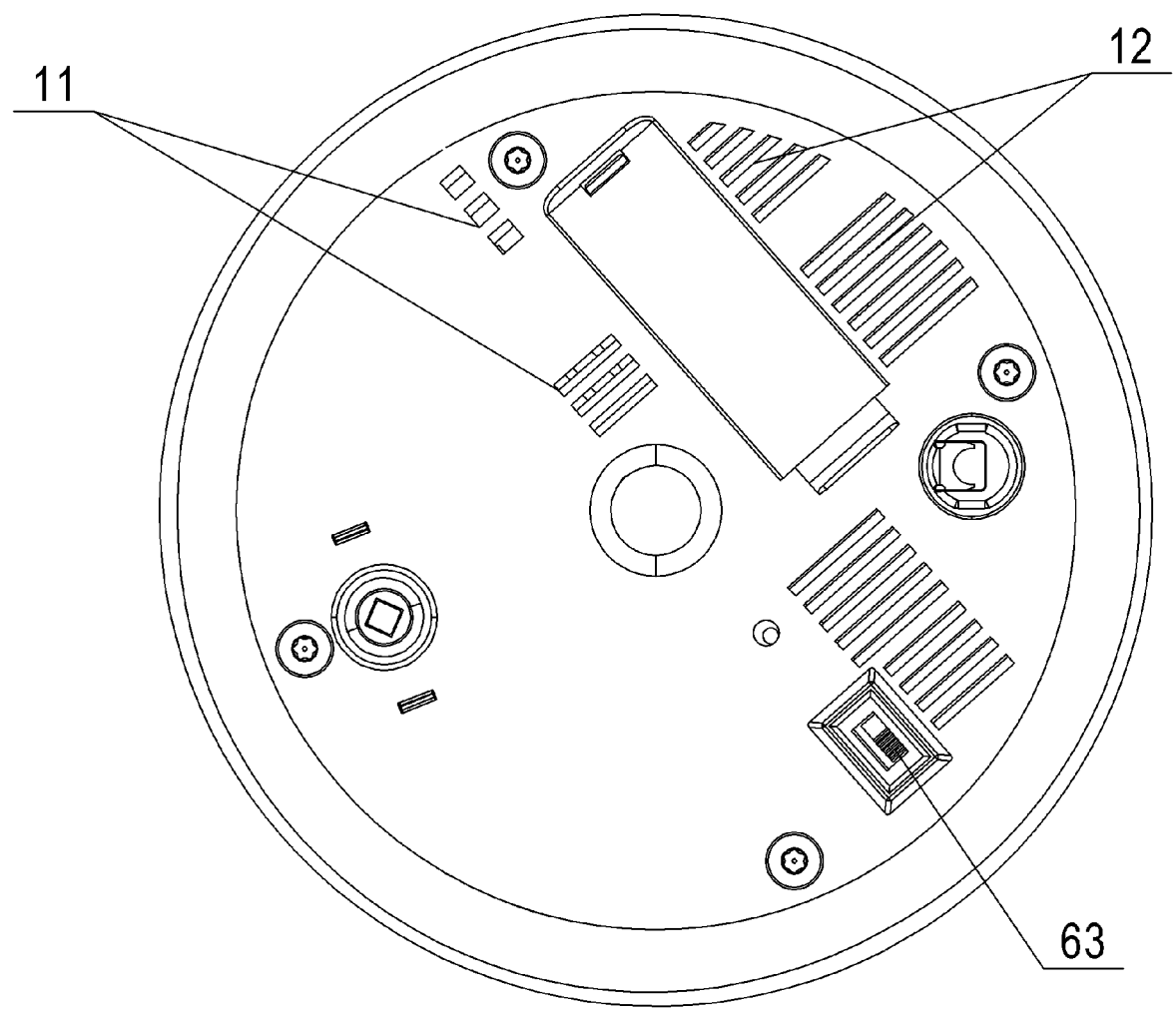
FIG. 4 is a schematic diagram showing a bottom surface of the bottom mounting housing of the sterilization control system of the waste disposer according to the present invention.
Figure 5:
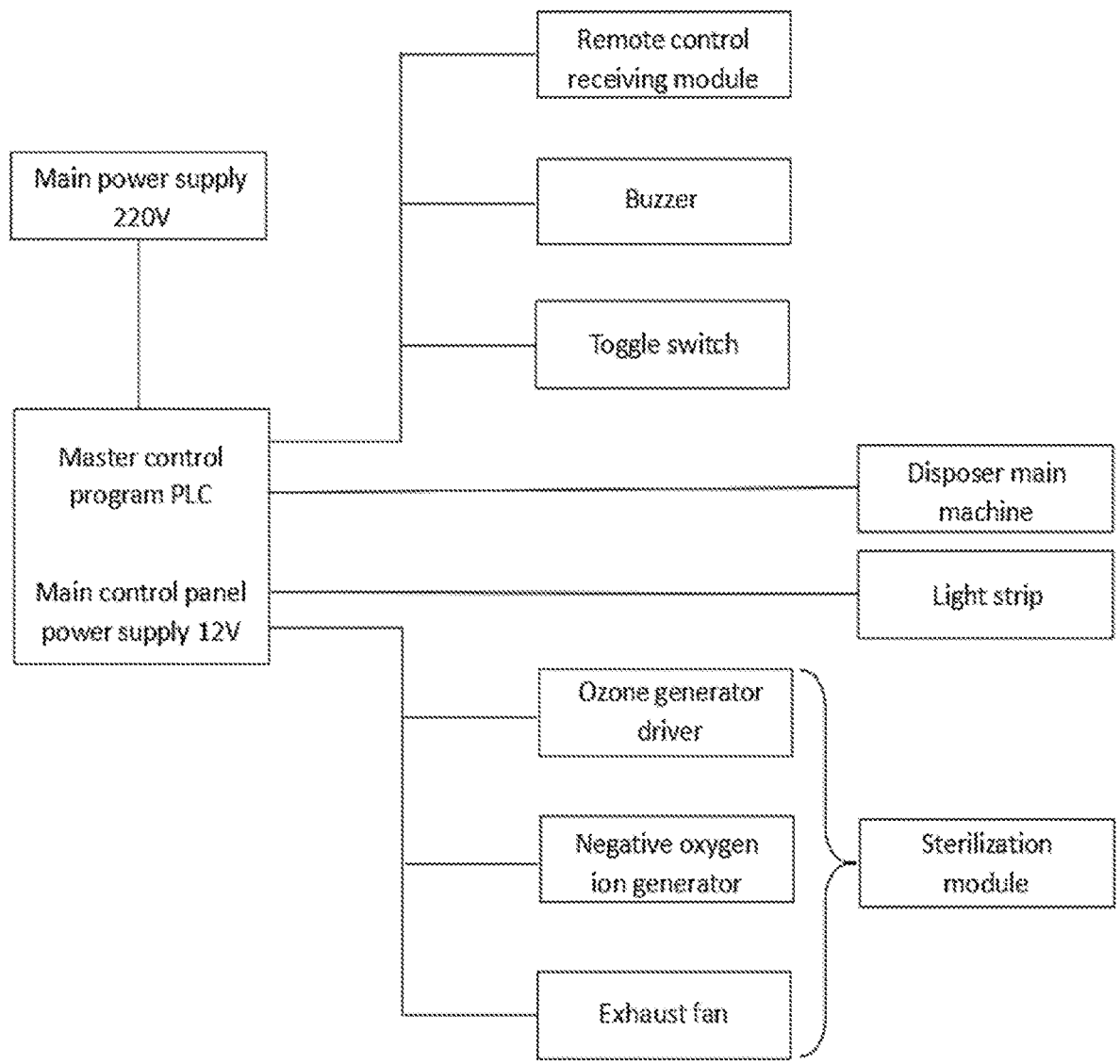
FIG. 5 is a schematic diagram showing circuit control of the sterilization control system of the waste disposer according to the present invention.

As shown in FIG. 1 to FIG. 4, a sterilization and air purification control system and a mounting structure of a waste disposer are provided. The sterilization and air purification control system includes a bottom mounting housing 1 and a disposer main machine 2 and further including a sterilization module 3. The sterilization module 3 includes an ozone generator driver 31, a negative oxygen ion generator 32 and an exhaust mechanism 33. The bottom mounting housing 1 is an accommodating housing and is detachably mounted at a bottom portion of the disposer main machine 2, and an outer edge of the bottom mounting housing 1 is provided with a light strip 4. The exhaust mechanism 33 is fixedly connected to an inside of one side surface of the bottom mounting housing 1, and the exhaust mechanism 33 communicates with inner and outer sides of the bottom mounting housing 1 A main control panel 5, an electric control subpanel 6, a starting capacitor 7 and the sterilization module 3 are mounted in the bottom mounting housing 1, and the electric control subpanel 6, the starting capacitor 7, the sterilization module 3 and the light strip 4 are all electrically connected to the main control panel 5.

The main control panel 5 is further connected with an overload protector 51, a fan power interface 52, a light strip power interface 53 and a motor power interface 54.

The electric control subpanel 6 includes a buzzer 61, a remote control receiving module 62 and a toggle switch 63, and the toggle switch 63 has three gears.

The three gears respectively represent "a sterilization function is switched off", "a remote control function is switched on or off", and "the sterilization function is switched on to remotely control the sterilization module 3 to be switched on or off".

The light strip 4 is connected to the light strip power interface 53 by a conductive wire, and the light strip 4 has three working modes including a blue marquee state, a green breath light state and a red constant light state.

When the disposer main machine 2 is started, the buzzer 61 makes a sound, and the light strip 4 enters the blue marquee state. After the disposer main machine 2 is halted, the overload protector 51 works, and the main control panel 5 controls a motor of the disposer main machine 2 to forwards and reversely rotate for five times and then stop. Then, the light strip 4 enters the red constant light state and is kept in the state for 1 minute, and meanwhile, the buzzer 61 constantly makes sounds for 1 minute. After the disposer main machine 2 is shut down, the light strip 4 enters the green breath light state, and when the sterilization module 3 is started, the buzzer 61 makes a sound and the sterilization module 3 runs for 5 minutes, wherein the interval time for second running is set as 8 hours.

The exhaust mechanism 33 includes an exhaust chamber 331, an exhaust fan 332 and an ozone generator cell 333. The exhaust fan 332 and the ozone generator cell 333 are both mounted in the exhaust chamber 331. The exhaust fan 332 is capable of taking air in the bottom mounting housing 1 out of the bottom mounting housing 1 through a first air outlet 11. The first air outlet 11 is located in a bottom surface, corresponding to the exhaust chamber 331, of the bottom mounting housing. The ozone generator cell 333 is electrically connected to the ozone generator driver 31, and the exhaust fan 332 is connected to the fan power interface 52 by a conductive wire.

A bottom surface, close to the negative oxygen ion generator 32, of the bottom mounting housing 1 is provided with a second air outlet 12.

Working principle is as follows. When the disposer main machine 2 is started, the buzzer 61 makes a sound, and the light strip 4 enters the blue marquee state. After the disposer main machine 2 is halted, the overload protector 51 works, the main control panel 5 controls the motor of the disposer main machine 2 to forwards and reversely rotate for five times and then stop. Then, the light strip 4 enters the red constant light state and is kept in the state for 1 minute, and meanwhile, the buzzer 61 constantly makes sounds for 1 minute for reminding. After the disposer main machine 2 is shut down, the light strip 4 enters the green breath light state. By using the toggle switch 63, a user may remotely control the switched on and off of the sterilization module 3 or directly turn off the sterilization function, and then, remote control is invalid, and the sterilization module 3 does not work. If the sterilization function is available, when the sterilization module 3 is started after the disposer main machine 2 is started, the buzzer 61 makes a sound and the sterilization module 3 runs for 5 minutes, wherein the interval time for second running is set as 8 hours.

The overall sterilization and air purification control system strictly controls the work time of ozone which is only allowed to work once to twice every day, and an ozone concentration sensor is additionally provided to intelligently monitor the concentration of the ozone, so that the aim for safe use is achieved. The negative oxygen ion generator plays roles in assisting in ozone sterilization and also purifying air to remove unpleasant odors.

With the above-mentioned ideal embodiments of the present invention as teachings, relevant staffs can completely make various alterations and modifications based on the above-mentioned description contents without departing from the scope of technical idea of the present invention. The technical scope of the present invention is not limited to the contents in the specification and has to be determined according to the scope of claims.

What is claimed is:

1. A sterilization and air purification control system and a mounting structure of a waste disposer, comprising a bottom mounting housing, a disposer main machine and a sterilization module, wherein the sterilization module comprises an ozone generator driver, a negative oxygen ion generator and an exhaust mechanism, the bottom mounting housing is an accommodating housing and is detachably mounted at a bottom portion of the disposer main machine, an outer edge of the bottom mounting housing is provided with a light strip, the exhaust mechanism is fixedly connected to an inside of one side surface of the bottom mounting housing, the exhaust mechanism communicates with inner and outer sides of the bottom mounting housing, a main control panel, an electric control subpanel, a starting capacitor and the sterilization module are mounted in the bottom mounting housing, and the electric control subpanel, the starting capacitor, the sterilization module and the light strip are all electrically connected to the main control panel.

2. The sterilization and air purification control system and a mounting structure of the waste disposer of claim 1, wherein the main control panel is connected with an overload protector, a fan power interface, a light strip power interface and a motor power interface.

3. The sterilization and air purification control system and a mounting structure of the waste disposer of claim 2, wherein the electric control subpanel comprises a buzzer, a remote control receiving module and a toggle switch, and the toggle switch has three gears.

4. The sterilization and air purification control system and a mounting structure of the waste disposer of claim 3, wherein the three gears respectively represent that "a sterilization function is switched off", "a remote control function is switched off or on", and "the sterilization function is switched on to remotely control the sterilization module to be switched on or off".

5. The sterilization and air purification control system and a mounting structure of the waste disposer of claim 4, wherein the light strip is connected to the light strip power interface by a conductive wire, and the light strip has three working modes comprising a blue marquee state, a green breath light state and a red constant light state.

6. The sterilization and air purification control system and a mounting structure of the waste disposer of claim 5, wherein when the disposer main machine is started, the buzzer makes a sound, and the light strip enters the blue marquee state; after the disposer main machine is halted, the overload protector works, the main control panel controls a motor of the disposer main machine to forwards and reversely rotate for five times and then stop, then, the light strip enters the red constant light state and is kept in the state for 1 minute, and meanwhile, the buzzer constantly makes sounds for 1 minute; and after the disposer main machine is shut down, the light strip enters the green breath light state, and when the sterilization module is started, the buzzer makes a sound and the sterilization module runs for 5 minutes, wherein an interval time for second running is set as 8 hours.

7. The sterilization and air purification control system and a mounting structure of the waste disposer of claim 2, wherein the exhaust mechanism comprises an exhaust chamber, an exhaust fan and an ozone generator cell, the exhaust fan and the ozone generator cell are both mounted in the exhaust chamber, the exhaust fan is capable of taking air in the bottom mounting housing out of the bottom mounting housing through a first air outlet, the first air outlet is located in a bottom surface, corresponding to the exhaust chamber, of the bottom mounting housing, the ozone generator cell is electrically connected to the ozone generator driver, and the exhaust fan is connected to the fan power interface by a conductive wire.

8. The sterilization and air purification control system and a mounting structure of the waste disposer of claim 1, wherein a bottom surface, close to the negative oxygen ion generator, of the bottom mounting housing is provided with a second air outlet.

9. The sterilization and air purification control system and a mounting structure of the waste disposer of claim 1, wherein the overall control system strictly controls work time of ozone which is only allowed to work once to twice every day, and an ozone concentration sensor is additionally provided to intelligently monitor concentration of the ozone.

10. The sterilization and air purification control system and a mounting structure of the waste disposer of claim 1, wherein the negative oxygen ion generator is configured for assisting in ozone sterilization and purifying air to remove unpleasant odors.

\* \* \* \* \*